(12) United States Patent
Chen et al.

(10) Patent No.: US 7,003,070 B1
(45) Date of Patent: Feb. 21, 2006

(54) UPRIGHT CT SCANNER

(76) Inventors: William Barry Chen, 3780 N. Firestone Dr., Hoffman Estates, IL (US) 60195; Jason Andrew Chen, 3780 N. Firestone Dr., Hoffman Estates, IL (US) 60195

( * ) Notice: Subject to any disclaimer, the term of this patent is extended or adjusted under 35 U.S.C. 154(b) by 0 days.

(21) Appl. No.: 10/911,782

(22) Filed: Aug. 3, 2004

(51) Int. Cl.
*A01B 6/04* (2006.01)
*A01B 6/03* (2006.01)

(52) U.S. Cl. .......................................... 378/17; 378/20
(58) Field of Classification Search ................ 378/4, 378/10, 11, 13, 17, 20
See application file for complete search history.

(56) References Cited

U.S. PATENT DOCUMENTS

| | | | |
|---|---|---|---|
| 4,134,020 A * | 1/1979 | Zonneveld ................. | 378/13 |
| 4,977,588 A * | 12/1990 | Van der Ende ............ | 378/17 |
| 5,042,487 A * | 8/1991 | Marquardt ................. | 378/17 |
| 6,148,058 A * | 11/2000 | Dobbs ........................ | 378/10 |
| 6,574,297 B1 * | 6/2003 | Tam ........................... | 378/15 |
| 2004/0258195 A1 * | 12/2004 | Hara .......................... | 378/11 |

FOREIGN PATENT DOCUMENTS

| JP | 2003126080 A | * | 5/2003 |
|---|---|---|---|
| WO | WO 200160258 A1 | * | 8/2001 |

* cited by examiner

*Primary Examiner*—Edward J. Glick
*Assistant Examiner*—Chih-Cheng Glen Kao

(57) ABSTRACT

In an upright CT scanner, an X-ray source and a two-dimensional digital X-ray detector are mounted on a rotating platform with a vertical axis of rotation. During scanning, the X-ray source and the detector are on opposite sides of the rotational axis for orbiting about a body to thereby scan it with pyramid-shaped X-ray beam. During scanning, the source and detector can be jointly translated along a horizontal axis that is perpendicular to the rotation axis and parallel to the detector surface, to scan a specific part of a body that is not centered or a body that is too large. The mounting height and distance of source and the detector can also be adjusted.

14 Claims, 3 Drawing Sheets

UPRIGHT CT SCANNER

STATEMENT REGARDING FEDERALLY SPONSORED RESEARCH

Not applicable.

BACKGROUND OF THE INVENTION

1. Field of Invention

This invention relates examining the human body with X-ray by means of computed tomography, and more specifically, to a tomography apparatus that allows a patient to be scanned with his torso upright.

2. Description of the Prior Art

X-ray computed tomography is one of the most frequently utilized modalities in diagnostic imaging. Recent developments in multi-slice CT technology have proven the diagnostic value of CT in areas such as cardiology. Since cardiovascular disease is currently the leading cause of death in the United States, it is desirable that cardiac CT scanners become a routine examination tool just as X-ray examinations have become, capable of being utilized in small hospitals, outpatient clinics, and doctors' offices. This requires a new generation of CT scanners that are more affordable, convenient to use, and able to detect minute abnormalities for early diagnosis.

In current commercially available multi-slice CT scanners, a patient must be laid on a bed. This is not the optimal position for to examine for cardiovascular diseases because when a patient is lying down, his organs take more relaxed positions and thus it becomes more difficult to detect minute abnormalities. In addition, eliminating the patient bed can reduce the overall cost of the machine. Therefore, an upright CT scanner is more suitable in cardiology. However, it is not possible to eliminate the bed for conventional CT scanners. This is because the bed translation, combined with the gantry rotation, forms a spiral trajectory, which is the foundation for the current narrow CT detector to continuously scan a section of body. In 1979, Richard T. Bemardi patented a hybrid scanner that scans in either vertical or horizontal positions in his U.S. Pat. No. 4,316,091. Practically, however, his design has safety concerns and is probably more expensive than conventional CT scanners.

With the advent of the digital X-ray detector, the use of 2D silicon detectors for CT scanners has been the subject of intensive research. Since one view of a 2D digital X-ray detector can cover the entire heart, the spiral motion of the conventional CT scanner is no longer necessary. One successful example is C-arm based CT, where an X-ray tube and a 2D digital X-ray detector are mounted at two ends of a C-arm. Despite many advantages of C-arm CT scanner, structural instability of C-arm during the oscillating rotation causes the problem of image registration. In addition, C-arm CT scanners may not be able to scan a large patient or part of body that is far from the axis of rotation center without a large, expensive detector.

SUMMARY OF THE INVENTION

The object of the present invention is to provide a unique upright CT scanner that produces clinical quality images and is affordable enough for use in small hospitals, outpatient clinics, and doctors' offices. Instead of lying on a bed, a patient is either seated or standing during the examination. The X-ray source and detector are mounted on a platform instead of a gantry, translating while rotating. The distance between the X-ray source and detector, as well as the height at which they operate, is adjustable. The distance adjustment is particularly desirable because X-ray dosage can be reduced when the detector in close proximity to the patient.

Several factors make the system affordable. Clearly the cost of the bed can be eliminated. Also, employment of the 2D digital X-ray detector eliminates the need for rapid rotation and thus the mechanical components and associated control systems are simplified. In addition, the step-and-shot scan mode of the detector makes it possible to utilize a pulse X-ray tube with less power, which reduces the cost of the tube as well as cooling and power generation systems. In addition, the small footprint of the invention reduces the cost associated with the installation, shielding and maintenance.

More importantly, the present invention brings a variety of clinical benefits. The unique upright patient position provides some clinical advantages, such as detecting small anomalies in cardiac imaging. The gantry-less design allows for safe and easy access for both the patient and medical personnel. The high-resolution digital X-ray detector and stable mechanical structure produce quality high-resolution CT images that exceed the image quality of even the most expensive current multi-slice CT scanners. Coupled with an EKG device, the present invention is particularly suitable for cardiac imaging, as the field of view can be centered at the heart and one view of the image is large enough to cover the entire heart. Finally, the present invention can be used as a radiography machine. The ability to take high-resolution radiographs and CT scans in a single setting is highly desirable for many examinations, particularly in the field of urology.

DESCRIPTION OF A PREFERRED EMBODIMENT

Figure 1:
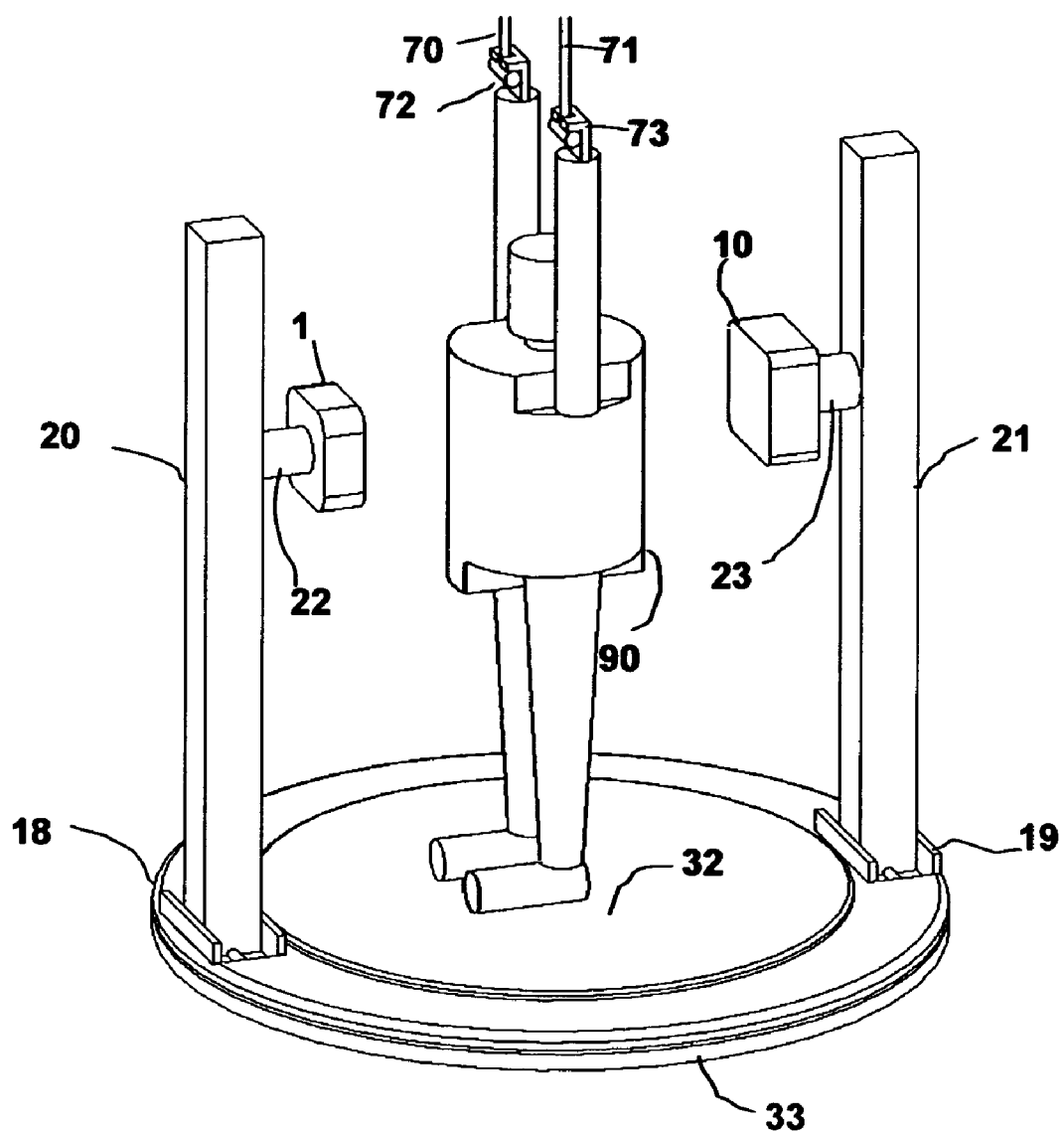
FIG. 1 is a perspective view of the present invention.

The principles of the invention will be discussed first in reference to FIG. 1. In this figure, patient 90 is standing on a stationary base platform 32 and holding handles 72 and 73, which are mounted to the ceiling by structures 70 and 71. The X-ray source is designated generally by the reference numeral 1. The two-dimensional digital X-ray detector is designated generally by the reference numeral 10. The X-ray source 1 is mounted to a horizontal linear motion mechanism 22, while the X-ray detector 10 is mounted to another horizontal linear motion mechanism 23. The combination of the linear motion from mechanisms 22 and 23 adjusts the distance between the X-ray source 1 and the detector 10. The mechanisms 22 and 23 can be controlled to move either individually or in tandem.

The linear motion mechanisms 22 and 23 are mounted to two vertical linear motion mechanisms, designated as columns 20 and 21, respectively. The joint motion provided by columns 20 and 21 adjusts the height of the X-ray source 1 and detector 10 simultaneously. The patient's size and the organ to be scanned determine the adjustments of the height and distance of X-ray source and detector. The distance adjustment allows the patient to be at the center of rotation while within the smallest safety circle during scanning. Here the safety-circle refers to a circle in which the patient will not interfere with any moving components. The adjustment should be done prior to scanning the patient.

The two columns 20 and 21 are mounted to a pair of linear motion mechanisms 18 and 19 that are fastened horizontally at the opposite sides of a diameter of rotating ring platform 33. The linear motion mechanisms 18 and 19 provide joint linear motion perpendicular to the diameter at which they are fastened. Rotating ring 33 provides X-ray source and detector assemblies with structural support and joint rotation around its center axis.

Figure 2:
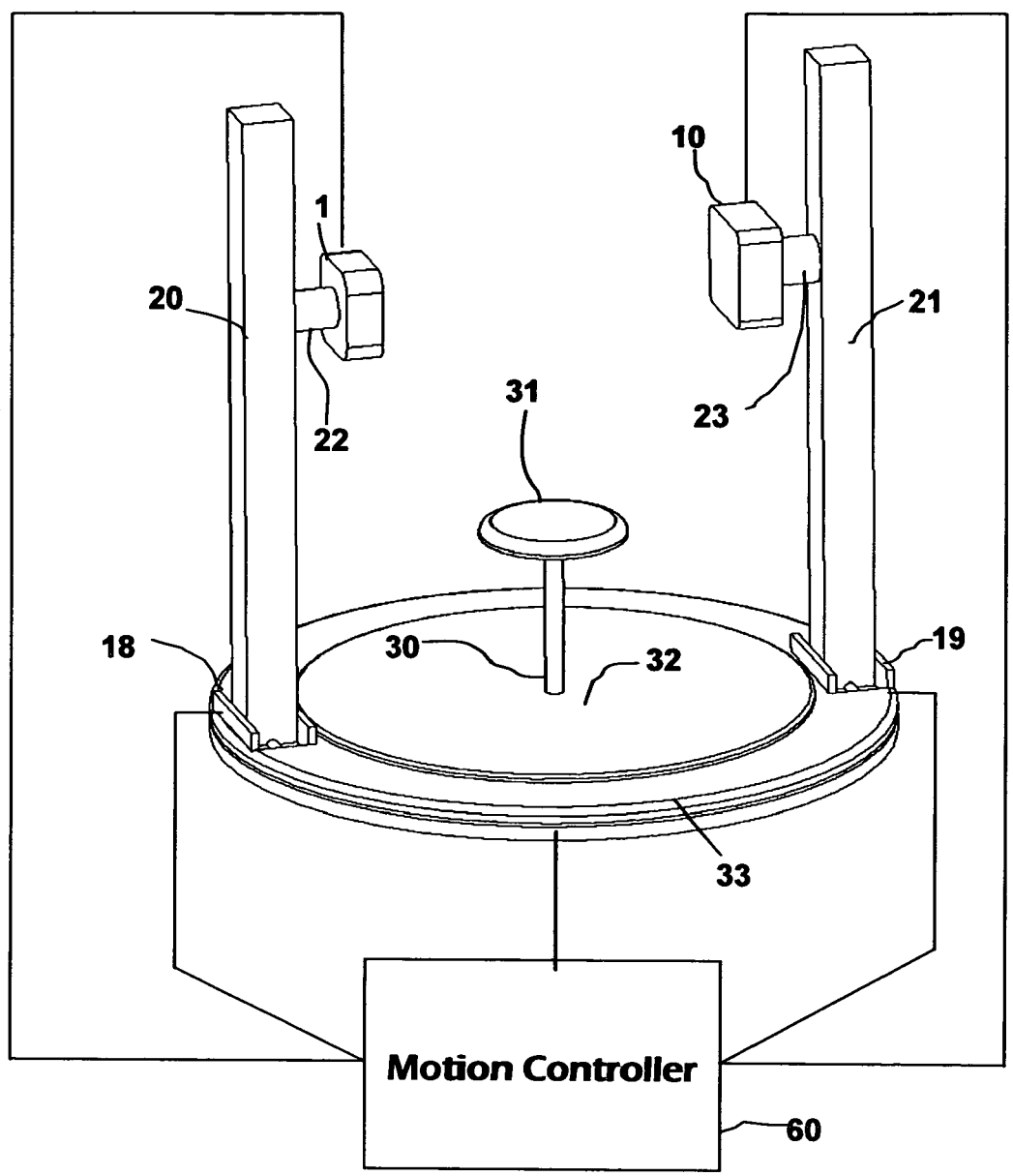
FIG. 2 is a diagram useful for explaining the principles of the invention.

Sometimes it is desirable that a patient is seated. FIG. 2 shows a removable or retractable sitting device 31 mounted on the base platform 32. The height of device 31 can be adjusted by column 30 to suit the needs of the patient.

During the scan, X-ray emission from X-ray source 1, data acquisition from detector 10, and motion from mechanisms 18, 19, and 33 are synchronized and coordinated by motion controller 60, as shown in FIG. 2. According to the motion of devices 18, 19, and 33 during the scan, the apparatus has three basic operation modes.

First, if there is no motion at all, then the apparatus serves as a conventional X-ray radiography machine.

Figure 3A:
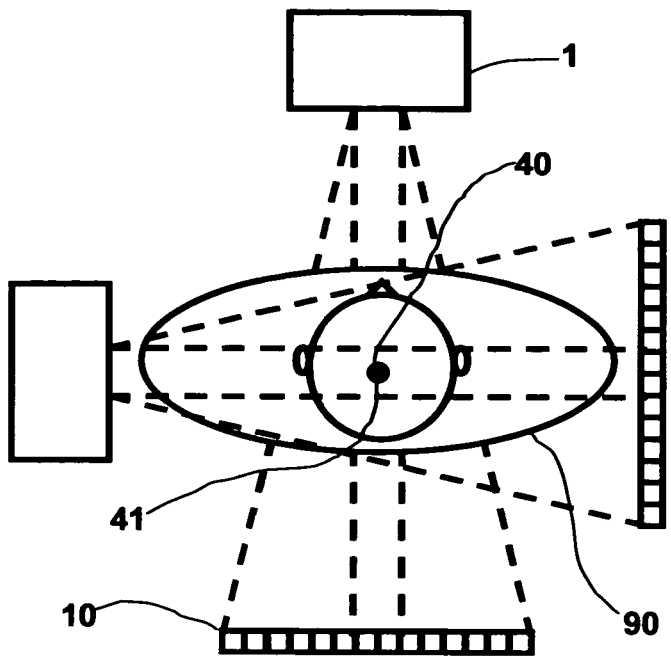
FIG. 3 illustrates X-ray source and detector configurations with two scan modes.

Second, if only 33 rotates while 18 and 19 are stationary, then the apparatus is similar to a conventional CT scanner with the center of field of view overlapped to the center of rotation. FIG. 3(a) illustrates the configuration of X-ray source 1 and detector 10 in this mode, where the reference numeral 40 denotes the center of rotation and reference numeral 41 the center of field of view. 40 and 41 are pointed to the same point.

Figure 3B:
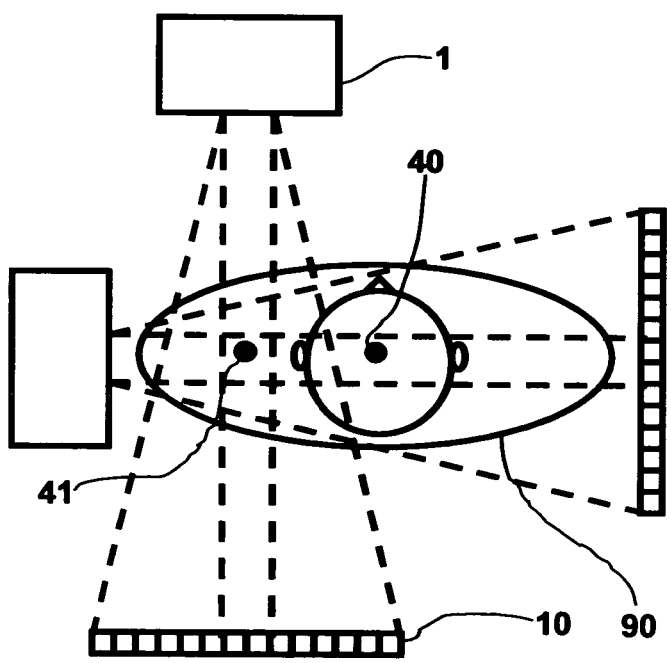

Third, if joint translations of 18 and 19 are provided in addition to the rotation of 33, then the apparatus can scan a patient with the instantaneous center of field of view (FOV) different from the instantaneous center of rotation, as illustrated in FIG. 3(b), where the center of rotation 40 and the center of field of view 41 are not the same. This mode also allows scanning an organ that is not centered or scanning a large patient with a small size of detector.

During scanning, the patient's hands can be in different positions according to the organ to be scanned and support needed to his body. In FIG. 1, a patient is holding handles 72 and 73 mounted to a ceiling. This is a desired position for a torso scan without the obstruction of arms, such as in the case of cardiac imaging. For a head scan however, it is more suitable that the patient's arms are held down to his side, in which case handles attached to the sitting device 31 or from base platform 32 are more suitable.

Although a particular embodiment of the invention has been described in some detail, such description is intended to be illustrative rather than limiting, for the invention may be variously embodied and is to be limited only by interpretation of the claims which follow.

The invention claimed is:

1. An upright CT scanning apparatus comprising:
   a. an X-ray source for projecting an X-ray pyramid-shaped beam originating substantially from a point;
   b. a two dimensional radiation detector arranged opposite to said X-ray source for detecting said X-ray beam emitted by said X-ray source;
   c. a ring platform below an upright patient for rotating said X-ray source and said radiation detector around a vertical system axis at an ISO center;
   d. mechanisms directly fastened to the ring platform for linearly translating said X-ray source and said radiation detector jointly along a horizontal axis parallel to a detector surface;
   e. a controller for coordinating the rotation, translation, and timing of X-ray source emission and detector data acquisition;
   f. mechanisms for adjusting a distance between said X-ray source and said radiation detector;
   g. mechanisms for adjusting a height of said X-ray source and said radiation detector jointly;
   h. and devices for positioning the upright patient disposed in said X-ray beam.

2. The upright CT scanning apparatus of claim 1 wherein said ring platform for rotating rotates about said vertical axis that is parallel to said detector surface and is parallel to a patient's torso.

3. The upright CT scanning apparatus of claim 1 wherein said mechanisms for linearly translating are mounted on said ring platform so that said X-ray source and said detector are able to jointly translate along said horizontal axis parallel to said detector surface and rotating about said vertical system axis.

4. The upright CT scanning apparatus of claim 1 wherein said controller for coordinating allows said X-ray source and detector to either rotate only or rotate rotating while translating, and wherein the controller for coordinating synchronizes said rotating and translating to the timing of X-ray source emission and detector data acquisition.

5. The upright CT scanning apparatus of claim 1 wherein said mechanisms for adjusting the distance allow said distance to be adjusted according to said patient size and to be maintained during a period of image acquisition said mechanisms for adjusting the distance also allow said distance to be adjusted so that said patient can safely enter and exit said scanning apparatus.

6. The upright CT scanning apparatus of claim 1 wherein said mechanisms for adjusting the height allow said height to be adjusted and to be maintained during a period of image acquisition, so that said X-ray source and said detector are centered at a region of interest (ROI) of said patient.

7. The upright CT scanning apparatus of claim 1 wherein said devices for positioning further comprise:
   a. a stationary platform on which said patient can stand or be seated;
   b. a sitting device that is removable or retractable;
   c. and adjustable holding devices mounted on a ceiling or on said sitting device to assist said patient to keep an upright position.

8. A method for use with an upright CT scanning apparatus comprising an X-ray source for projecting an X-ray pyramid-shaped beam originating substantially from a point; a two dimensional radiation detector arranged opposite to said X-ray source for detecting said X-ray beam emitted by said X-ray source; a ring platform below a patient for rotating said X-ray source and said radiation detector around a vertical system axis at an ISO center; mechanisms directly fastened to the ring platform for linearly translating said X-ray source and said radiation detector jointly along a horizontal axis parallel to a detector surface; a controller for coordinating the rotation, translation, and timing of X-ray source emission and detector data acquisition; mechanisms for adjusting a distance between said X-ray source and said radiation detector; mechanisms for adjusting a height of said X-ray source and said radiation detector jointly; and devices for positioning an upright patient disposed in said X-ray beam, the method comprising the steps of:
   a. adjusting said height and said distance between said X-ray source and said detector;
   b. disposing the patient to said X-ray beam in an upright position;

c. rotating and translating of said X-ray source and said detector during scanning;

d. emitting said X-ray beam with said sources and acquiring data with said detector.

9. The method for use with an upright CT scanning apparatus of claim 8 wherein said adjusting the height of the X-ray source and detector allows height to be the same as a height of a center of an ROI of the patient; and adjusting said distance between said X-ray source and said detector allows said patient to be at a center of rotation while within the smallest safety circle during scanning, and wherein the patient within the circle will not interfere with moving components, said height and distance being maintained during a period of image acquisition.

10. The method for use with an upright CT scanning apparatus of claim 8 wherein disposing a patient disposed to said X-ray beam in an upright position is supported with mounted handles.

11. The method for use with an upright CT scanning apparatus of claim 8 wherein the rotating and translating are determined according to scan modes.

12. The method for use with an upright CT scanning apparatus of claim 11 wherein the scan modes include both rotating and translating being equal to zero.

13. The method for use with an upright CT scanning apparatus of claim 11 wherein the scan modes include rotating at a constant speed and translating being equal to zero.

14. The method for use with an upright CT scanning apparatus of claim 11 wherein the scan modes include rotating at a constant speed and translating can be describes as a function of rotation angle.

* * * * *